(12) United States Patent
Yen (10) Patent No.: US 7,233,817 B2
(45) Date of Patent: Jun. 19, 2007

(54) APPARATUS AND METHOD FOR PATTERN DELIVERY OF RADIATION AND BIOLOGICAL CHARACTERISTIC ANALYSIS

(76) Inventor: Brian Yen, 650 La Mesa Dr., Portola Valley, CA (US) 94028

( * ) Notice: Subject to any disclaimer, the term of this patent is extended or adjusted under 35 U.S.C. 154(b) by 601 days.

(21) Appl. No.: 10/682,655

(22) Filed: Oct. 8, 2003

(65) Prior Publication Data

US 2004/0087844 A1 May 6, 2004

Related U.S. Application Data

(60) Provisional application No. 60/423,345, filed on Nov. 1, 2002.

(51) Int. Cl.
*A61B 5/00* (2006.01)
(52) U.S. Cl. ........................ 600/319; 600/322
(58) Field of Classification Search ................ 600/310, 600/316, 318, 319, 320, 321, 322, 323, 340, 600/473, 476; 351/205, 206, 209
See application file for complete search history.

(56) References Cited

U.S. PATENT DOCUMENTS

| | | |
|---|---|---|
| 3,958,560 A | 5/1976 | March |
| 4,169,676 A | 10/1979 | Kaiser |
| 5,028,787 A | 7/1991 | Rosenthal et al. |
| 5,178,142 A | 1/1993 | Harjunmaa et al. |
| 5,179,951 A | 1/1993 | Knudson |
| 5,219,400 A * | 6/1993 | Jacot et al. ............. 600/320 |
| 5,240,006 A | 8/1993 | Fujii et al. |
| 5,267,152 A | 11/1993 | Yang et al. |
| 5,313,941 A | 5/1994 | Braig et al. |
| 5,398,681 A | 3/1995 | Kupershmidt |
| 5,433,197 A | 7/1995 | Stark |
| 5,517,313 A | 5/1996 | Colvin, Jr. |
| 5,549,596 A | 8/1996 | Latina |
| 5,640,963 A * | 6/1997 | Tanaka ..................... 600/318 |
| 5,692,504 A | 12/1997 | Essenpreis et al. |
| 5,710,630 A | 1/1998 | Essenpreis et al. |
| 5,857,462 A | 1/1999 | Thomas et al. |
| 5,871,442 A | 2/1999 | Madarasz et al. |
| 5,894,337 A | 4/1999 | Okinishi et al. |
| 5,957,841 A | 9/1999 | Maruo et al. |

(Continued)

FOREIGN PATENT DOCUMENTS

CN 1201905 A 12/1998

(Continued)

OTHER PUBLICATIONS

Freiherr, Greg; "*The Race to Develop a Painless Blood Glucose Monitor*"; R&D Horizons, Medical Device & Diagnostic Industry (MDDI) archive; Mar. 1997; 9 pages.

(Continued)

*Primary Examiner*—Eric F. Winakur
(74) *Attorney, Agent, or Firm*—Thelen Reid Brown Raysman & Steiner; Aaron Wininger (57) ABSTRACT

The present invention uses a high signal to noise ratio method and apparatus to analyze a characteristic of a biological object, such as blood glucose level. The method and apparatus can also have surgical applications, such as coagulation or ablation of a pattern on a biological object.

10 Claims, 5 Drawing Sheets

U.S. PATENT DOCUMENTS

| | | | |
|---|---|---|---|
| 6,001,067 | A | 12/1999 | Shults et al. |
| 6,025,597 | A | 2/2000 | Sterling et al. |
| 6,026,314 | A | 2/2000 | Amerov et al. |
| 6,028,311 | A | 2/2000 | Sodickson et al. |
| 6,061,582 | A | 5/2000 | Small et al. |
| 6,064,898 | A | 5/2000 | Aldrich |
| 6,066,847 | A | 5/2000 | Rosenthal |
| 6,072,180 | A | 6/2000 | Kramer et al. |
| 6,097,975 | A | 8/2000 | Petrovsky et al. |
| 6,099,522 | A | 8/2000 | Knopp et al. |
| 6,104,939 | A | 8/2000 | Groner et al. |
| 6,113,537 | A | 9/2000 | Castano |
| 6,120,460 | A | 9/2000 | Abreu |
| 6,151,522 | A | 11/2000 | Alfano et al. |
| 6,152,875 | A | 11/2000 | Hakamata |
| 6,161,028 | A | 12/2000 | Braig et al. |
| 6,167,290 | A | 12/2000 | Yang et al. |
| 6,172,743 | B1 | 1/2001 | Kley et al. |
| 6,181,957 | B1 | 1/2001 | Lambert et al. |
| 6,188,477 | B1 | 2/2001 | Pu et al. |
| 6,213,943 | B1 | 4/2001 | Abreu |
| 6,222,189 | B1 | 4/2001 | Misner et al. |
| 6,246,893 | B1 | 6/2001 | Gobeli |
| 6,275,726 | B1 | 8/2001 | Chan et al. |
| 6,276,798 | B1 | 8/2001 | Gil et al. |
| 6,302,850 | B1 * | 10/2001 | Tsukada ............... 600/318 |
| 6,305,804 | B1 | 10/2001 | Rice et al. |
| 6,312,393 | B1 | 11/2001 | Abreu |
| 6,362,144 | B1 | 3/2002 | Berman et al. |
| 6,387,059 | B1 | 5/2002 | Marchitto et al. |
| 6,394,999 | B1 | 5/2002 | Williams et al. |
| 6,413,251 | B1 | 7/2002 | Williams |
| 6,421,548 | B1 | 7/2002 | Berman et al. |
| 6,423,001 | B1 | 7/2002 | Abreu |
| 6,424,848 | B1 | 7/2002 | Berman et al. |
| 6,424,851 | B1 | 7/2002 | Berman et al. |
| 6,430,424 | B1 | 8/2002 | Berman et al. |
| 6,574,501 | B2 * | 6/2003 | Lambert et al. ........ 600/473 |
| 2003/0120325 | A1 | 6/2003 | Shinichi et al. |

FOREIGN PATENT DOCUMENTS

| | | |
|---|---|---|
| EP | 0 279 589 A1 | 8/1988 |
| EP | 0 880 941 A1 | 12/1998 |
| EP | 0 933 096 A2 | 8/1999 |
| WO | WO 01/83030 A1 | 11/2001 |
| WO | WO 02/071932 A1 | 9/2002 |

OTHER PUBLICATIONS

"Continuous Monitoring of Blood Glucose Levels"; Animas Corporation; Products—Glucose Sensor; 4 pages; Copyright 2000, 2001.
Tuchin, Valery V.; "Coherence and Light Scattering Methods and Instruments for Medical Diagnosis"; SPIE'S Photonics West Biomedical Optics 2001 Conference; San Jose Convention Center; San Jose, CA; Jan. 20-26, 2001; Short Course Notes SC032; 15 pages.
Bashkatov, Alexey N. et al.; "Estimation of Glucose Diffusion Coefficient in Scleral Tissue"; 13 pages.
Klonoff, Dr. David C. et al.; "Mid-Infrared Spectroscopy for Noninvasive Blood Glucose Monitoring"; LEOS Newsletter; 3 pages; vol. 12, No. 2.
Waynant, R. W., Ph.D. et al.; "Overview of Non-Invasive Fluid Glucose Measurement Using Optical Techniques to Maintain Glucose Control in Diabetes Mellitus"; Overview of Non-Invasive Optical Glucose Monitoring Techniques; LEOS Newsletter; Apr. 1998; 5 pages; vol. 12, No. 2.
Medical Library—Noninvasive Blood Glucose Monitors; Medem, Inc.; 4 pages.
Digital Light Microscopy; Digital Optical Imaging Corp.; Copyright 1999-2002; 1 page.
"Creating a window into the body"; Posted Oct. 6, 2000; 2 pages. URL://http://perl.spie.org/cgi-bin/news.pl?id=1753.
Harding, Anne; "Jab-Free Blood Sugar Test Inching Closer to Reality"; Yahoo! News—Reuters Limited; Aug. 19, 2002; 3 pages.
Tamada, Janet A., Ph.D. et al.; "Noninvasive Glucose Monitoring Comprehensive Clinical Results"; JAMA; Nov. 17, 1999; pp. 1839-1844; vol. 282, No. 19; Copyright 1999 American Medical Association.
Hopkins, George W. et al.; "In-vivo NIR Diffuse-reflectance Tissue Spectroscopy of Human Subjects" HP Laboratories Palo Alto; Jan. 1999; HPL-1999-13; Copyright Hewlett-Packard Company 1999; 10 pages.
Ham, Fredric M., et al. "Multivariate determination of glucose concentrations from optimally filtered frequency-warped NIR spectra of human blood serum", Physiol, Meas. 17 (1996); pp. 1-20.
Kohl, Matthias et al. "The influence of glucose concentration upon the transport of light in tissue-simulating phantoms"; Phys. Med. Biol. 40 (1995); pp. 1267-1287.
GlucoWATCH—Automatic Glucose Biographer and Autosensors—Patient Information; Revision date Mar. 2001; Copyright Cygnus, Inc. 2000; 6 pages.
Pu, Chuan et al.; "A Surface-Micromachined Optical Self-Homodyne Polarimetric Sensor for Noninvasive Glucose Monitoring"; IEEE Photonics Technology Letters, Feb. 2000, pp. 190-192; Vo. 12, No. 2.
Savage, Mark B. et al.; "Development of a Non-invasive Blood Glucose Monitor: Application of Artificial Neural Networks for Signal Processing"; pp. 29-20; Copyright 2000 IEEE.
McShane, Michael J. et al.; "Glucose Monitoring Using Implanted Fluorescent Microspheres—Working Toward a Minimally Invasive Means for Diabetics to Better Monitor Glucose Levels"; IEEE Engineering in Medicine and Biology; Nov./Dec. 2000; pp. 36-45.
Ham, Fredric M.; "Multivariate Determination of Glucose Using NIR Specta of Human Blood Serum"; pp. 818-819; Copyright 1994 IEEE.
Olesberg, Jonathon T.; "Noninvasive blood glucose monitoring in the 2.0-2.5 $\mu m$ wavelength range"; Department of Chemistry and the Optical Science and Technology Center, University of Iowa, Iowa City, IA; p. 529; Copyright 2001 IEEE.
Yoon, Gilwon et al.; "Non-invasive Monitoring of Blood Glucose"; FP3 (Invited)/CLEO/Pacific Rim '99; p. 1233-1234; Copyright 1999 IEEE.
Yoon, Gilwon et al.; "Optical Measurement of Glucose Levels in Scattering Media"; Proceedings of the 20$^{th}$ Annual International Conference of the IEEE Engineering in Medicine and Biology Society; 1998; pp. 1897-1899; vol. 20, No. 4.
Yoon, Gilwon et al.; "Reagentless/Non-Invasive Diagnosis of Blood Substances"; MJ1-1 (Invited); pp. I-226-I-227.
Jiang, Desheng et al.; "Study on a New Fiber Optic Glucose Biosensor"; ThP9; pp. 451-454; Copyright 2002 IEEE.
Heise, H. M. et al.; "Technology for Non-Invasive Monitoring of Glucose"; 18$^{th}$ Annual International Conference of the IEEE Engineering in Medicine and Biology Society, M6 Minisymposium; Amsterdam 1996; pp. 2159-2161.
Colvin, Arthur E. et al.; "A Novel Solid-State Oxygen Sensor"; John Hopkins APL Technical Digest; 1996; pp. 377-385; vol. 17, No. 4.
Ameen, David B. et al.; "A Lattice Model for Computing the Transmissivity of the Cornea and Sclera"; Biophysical Journal; Nov. 1998; pp. 2520-2531; vol. 75.
Borchert, Mark S. et al.; "A Noninvasive Glucose Monitor: Preliminary Results in Rabbits"; Diabetes Technology & Therapeutics; 1999; pp. 145-151; vol. 1, No. 2; Mary Ann Liebert, Inc.
Hoerauf, H. et al.; "First experimental and clinical results with transscleral optical coherence tomography"; Opthalmic Surg Lasers May-Jun. 2000; PubMed; 2 pages.
Myers, J. S. et al.; "Laser energy reaching the posterior pole during transscleral cyclophotocoagulation"; Arch Opthalmol; Apr. 1998; PubMed; 2 pages.
Zheng, Peng, Ph.D. et al.; "Noninvasive Glucose Determination by Oscillating Thermal Gradient Spectrometry"; Diabetes Technology & Therapeutics; 2000; pp. 17-25; vol. 2, No. 1; Mary Ann Liebert, Inc.

Arnold, Mark A. Ph.D.; Editorial: "*Noninvasive Laser Measurement of Blood Glucose in the Eye: A Bright Idea or an Optical Illusion?*"; Diabetes Technology & Therapeutics; 1999; pp. 117-119; vol. 1, No. 2; Mary Ann Liebert, Inc.

Malin, Stephen F. et al.; "*Noninvasive Prediction of Glucose by Near-Infrared Diffuse Reflectance Spectroscopy*"; Clinical Chemistry; 1999; pp. 1651-1658; vol. 45, No. 9; Oak Ridge Conference.

Hammer, M. et al.; "*Optical properties of ocular fundus tissues—an in vitro study using the double-integrating-sphere technique and inverse Monte Carlo simulation*"; Phy Med Biol; Jun. 1995; 2 pages.

Preussner, P.R. et al.; "*Steps to optimize transscleral photocoagulation*"; Graefes Arch Clin Exp Opthalmol; May 1995; 2 pages.

Cameron, Brent D. et al.; "*The Use of Polarized Laser Light Through the Eye for Noninvasive Glucose Monitoring*"; Diabetes Technology & Therapeutics; 1999; pp. 135-143; vol. 1, No. 2; Mary Ann Liebert, Inc.

Small, Gary W. et al.; "*Data Handling Issues for Near-Infrared Glucose Measurements*"; LEOS Newsletters; Apr. 1998; 4 pages; vol. 12, No. 2.

McNichols, Roger J. et al.; "*Development of a Non-invasive Polarimetric Glucose Sensor*"; LEOS Newsletter; Apr. 1998; 3 pages; vol. 12, No. 2.

Heise, H. M.; "*Diffuse Reflectance Near-Infrared Spectrometry for Non-Invasive Blood Glucose Monitoring*"; LEOS Newsletter; Apr. 1998; 3 pages; vol. 12, No. 2.

Asher, Sanford A. et al.; "*Glucose Sensing Intelligent Polymerized Crystalline Colloidal Arrays*"; LEOS Newsletter; Apr. 1998; 4 pages; vol. 12, No. 2.

Burmeister, Jason J. et al.; "*Infrared Spectroscopy: Spectroscopic Considerations for Noninvasive Blood Glucose Measurements with Near Infrared Spectroscopy*"; LEOS Newsletter; Apr. 1998; 5 pages; vol. 12, No. 2.

Koo, Tae-Woong, et al.; "*Measurement of Glucose in Human Blood Serum Using Raman Spectroscopy*"; LEOS Newsletter; Apr. 1998; 2 pages; vol. 12, No. 2.

Lambert, James et al.; "*Measurement of Physiologic Glucose Levels Using Raman Spectroscopy in a Rabbit Aqueous Humor Model*"; LEOS Newsletter; Apr. 1998; 6 pages; vol. 12, No. 2.

Danzer, K. et al.; "*Near-Infrared Diffuse Reflection Spectroscopy for Non-Invasive Blood-Glucose Monitoring*"; LEOS Newsletter; Apr. 1998; 3 pages; vol. 12, No. 2.

Jang, Sunghoon, et al.; "*Optical Sensor Using the Magnetic Optical Rotatory Effect of Glucose*"; LEOS Newsletter; Apr. 1998; 4 pages; vol. 12, No. 2.

Tarr, Randall V. et al.; "*Non-Invasive Measure of D-Glucose in the Ocular Aqueous Humor using Stimulated Raman Spectroscopy*"; LEOS Newsletter, Apr. 1998; 10 pages; vol. 12, No. 2.

Khalil, Omar S.; "*Spectroscopic and Clinical Aspects of Noninvasive Glucose Measurements*"; Clinical Chemistry; 1999; pp. 165-177; vol. 45, No. 2.

Shichiri, Motoaki et al.; "*Non-invasive Fourier Transformed Infrared Spectroscopy for the Measurement of Submucosal Tissue Glucose Concentration—Application of Chalcogenide Optical Fiber System*"; LEOS Newsletter, Apr. 1998, 2 pages; vol. 12, No. 2.

McDonald, William et al.; "*Micron Sized Glucose Sensors for In-Vitro Monitoring of Glucose in Interstitial Fluid*"; LEOS Newsletter, Apr. 1998; 4 pages; vol. 12, No. 2.

McNamara, Kerry P. et al.; "*Optochemical Glucose Sensing in Volume Limited Samples*"; LEOS Newsletter, Apr. 1998; 3 pages; vol. 12, No. 2.

Larin, Kirill et al.; "*Optoacoustic Monitoring of Glucose Concentration in Ocular Tissues*"; Optoacoustic Imaging and Spectrocopy Laboratory, Biomedical Engineering Center, Department of Opthalmology; University of Texas Medical Branch, Galveston, Texas; Oct. 4, 1998; 26 pages.

\* cited by examiner

APPARATUS AND METHOD FOR PATTERN DELIVERY OF RADIATION AND BIOLOGICAL CHARACTERISTIC ANALYSIS

PRIORITY REFERENCE TO PRIOR APPLICATIONS

This application claims benefit of and incorporates by reference U.S. patent application Ser. No. 60/423,345, entitled "System and Method for Pattern Delivery of Radiation and Glucose Detection," filed on Nov. 1, 2002, by inventor Brian Yen.

TECHNICAL FIELD

This invention relates generally to radiation delivery and characteristic analysis, and more particularly, but not exclusively, provides a system and method for characteristic analysis using pattern delivery of radiation to a biological object.

BACKGROUND

Diabetes is a disease of the pancreas in which the pancreas produces little or no insulin or when the body does not respond properly to insulin ("insulin resistance"). There is no cure for diabetes and diabetics must generally manage the disease on a daily basis. One aspect of management includes injecting insulin, such as Lantus, multiple times a day or dispensing it continuously via a pump. Improper administration of insulin can lead to severe side effects including hyperglycemia in which blood glucose levels are too high, which can lead to damage to nerves, blood vessels, and other body organs. Improper administration can also lead to hypoglycemia, in which blood glucose levels are too low, which can lead to passing out and even coma in worst case scenarios. Accordingly, as the amount of insulin dispensed needs to be varied based on blood glucose levels, diabetics must frequently monitor their blood glucose levels.

Conventionally, home glucose monitoring is performed using a glucose blood meter, which yields results within a few minutes. In order to determine a blood glucose level, a person must first prick his or her finger with a small needle to collect a small amount of blood; the blood must then be placed on a test strip and inserted into the glucose test meter, which analyzes the blood for a blood glucose level. A diabetic can then adjust the amount of insulin to be dispensed accordingly.

A disadvantage of the conventional method of glucose monitoring is that it requires the drawing of blood, which can be painful and inconvenient. Accordingly, as glucose monitoring is extremely important for diabetics because of the risk of side effects, a new glucose monitoring system and method is needed that is non-invasive and pain free.

SUMMARY

Embodiments of the invention provide a system and method for non-invasive monitoring of blood glucose levels. Embodiments of the invention can also be used for the analysis of other properties of biological and/or non-biological objects. Further, embodiments of the invention can be used for pattern delivery of radiation, for example, in cosmetic surgery such as tattoo removal or varicose vein removal.

In one embodiment of the invention, a method comprises: detecting a pattern on the biological object; emitting radiation onto the detected pattern; collecting at least a portion of radiation that is reflected by the pattern on the object; and analyzing the collected radiation to determine a characteristic of the biological object.

An apparatus to carry out the method comprises an imaging detector, a mirror, a radiation emitter, a radiation detection assembly, and electronics. The imaging detector is positioned to receive a first type of reflected radiation from the biological object. The mirror is adjustable to reflect radiation onto a pattern on the object. The radiation emitter is capable of emitting radiation of a second type and positioned to emit the second type of radiation onto the mirror. The radiation detection assembly is positioned to receive reflected radiation of the second type from the biological object. The electronics, which is coupled to the imaging detector, radiation emitter, mirror and radiation detection assembly, is capable of identifying a pattern on the object using reflected radiation data from the imaging detector; adjusting the mirror to reflect the second type of radiation onto the identified pattern; and analyzing a characteristic of the object using reflected radiation data from the radiation detection assembly.

Accordingly, the apparatus and method provide a high signal to noise ratio without the need for high energy levels by using directed radiation, thereby avoiding interference problems.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those of ordinary skill in the art, and the principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
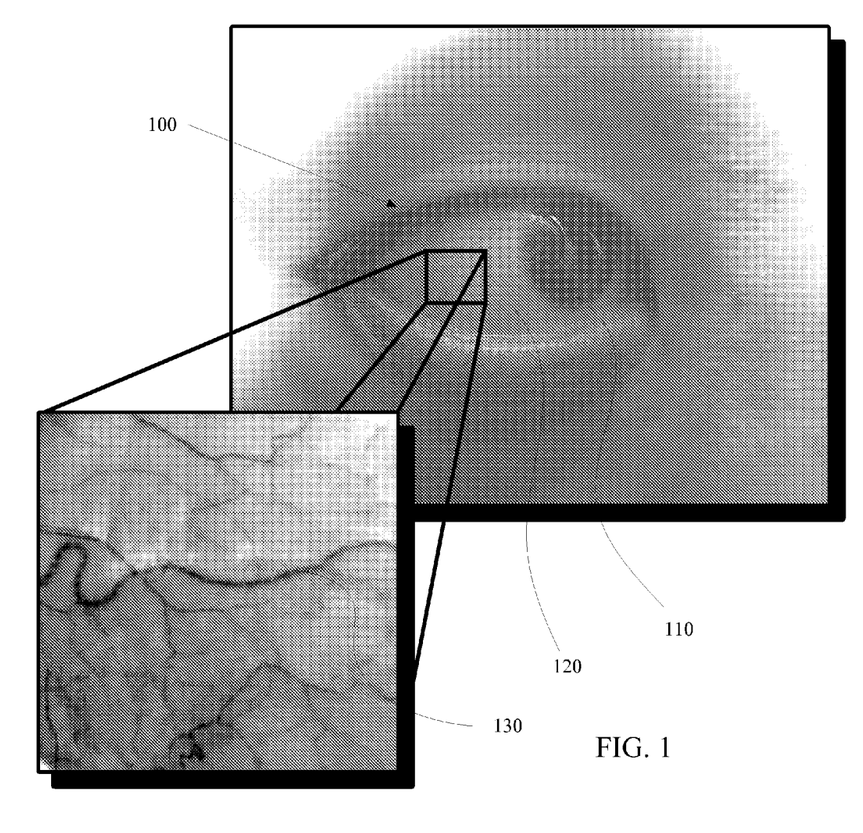
FIG. 1 is a depiction of an eye.

FIG. 1 is a depiction of an eye 100. The eye 100 is approximately 2.5 cm wide by 2.5 cm deep, with a height of 2.3 cm. The outer layer 120 of the eye is called the sclera and the approximately ⅙ of the sclera that is clear and exposed is referred to as the cornea. Extraocular muscles are coupled to the sclera and move the eye 100. The colored region 110 is the pupil of the eye 100 and is located in a second layer (i.e., choroid) of the eye 100 beneath the sclera 120. The choroid and the sclera 120 include a plurality of blood vessels, such as blood vessel 130, that supply blood to different regions of the eye. Generally, the blood vessels in the sclera 120 are the blood vessels in the body that are the most directly exposed to radiation. Accordingly, non-invasive analyte detection via spectrum analysis of blood is most easily and accurately performed using the blood vessels of the eyes. The blood vessels in the sclera 120 generally follow a non-linear path within the sclera and have varying thicknesses.

Figure 2:
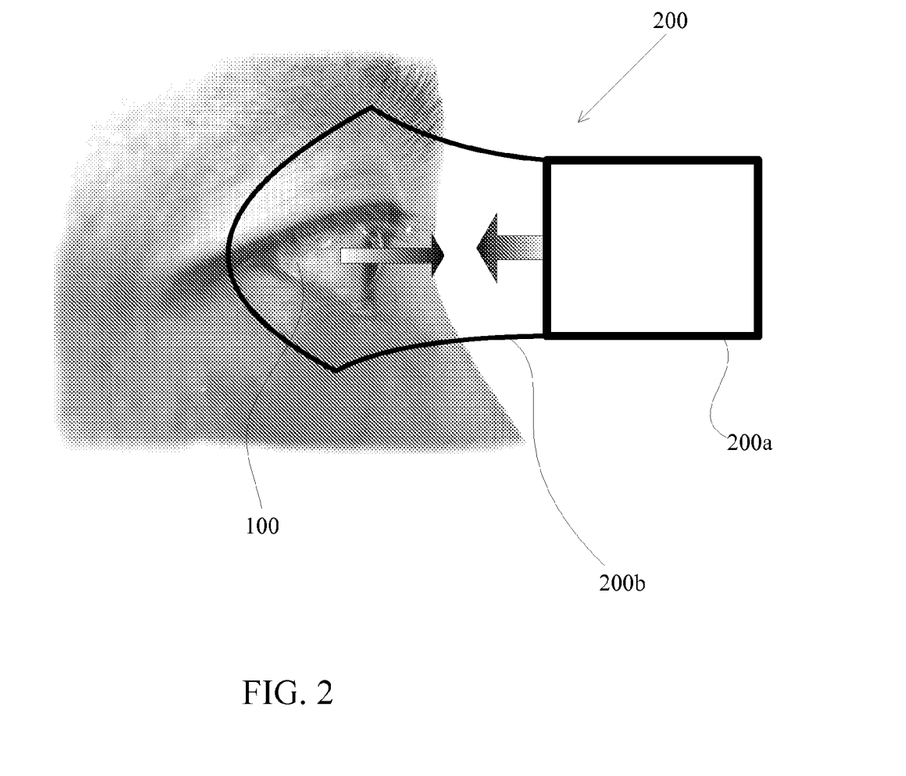
FIG. 2 is a diagram illustrating a device capable of pattern detection and pattern delivery of radiation.

FIG. 2 is a diagram illustrating a device 200 capable of detecting a pattern on the eye 100 and then delivering radiation to the eye 100 that coincides with the pattern. For example, the device 200 can detect the blood vessel 130 and deliver radiation that is coincident with the blood vessel 130 of the eye 100. In an embodiment of the invention, the device 200 can detect a pattern on any object and then deliver pattern radiation to that object, regardless of whether the object is of biological or non-biological origin. For example, the device 200 can detect the pattern of a grain of wood and then deliver pattern radiation such that the radiation is coincident with that grain of the wood. In an alternative example, the device 200 can detect a stress fracture pattern of an aluminum aircraft wing and deliver pattern radiation to the aluminum skin of the aircraft wing such that it is coincident with the stress fracture pattern. In another embodiment of the invention, the device 200 can deliver radiation that is coincident with an area surrounding or near to the pattern.

In an embodiment of the invention, the device 200 can also select a pattern or a set of patterns according to preset parameters if the object has a plurality of patterns. For example, the device 200 can select the blood vessel 130 in the eye 100 based on thickness, length, and/or color (e.g., red).

In another embodiment of the invention, the device 200 determines (e.g., detects and/or measures) characteristics of an object by performing a spectrum analysis of radiation radiated by the pattern, using reflective spectroscopy from reflected radiation from radiation incident on the pattern and/or using transmissive spectroscopy from diffuse radiation on an area surrounding or near the pattern. (Hereinafter, the term "radiated radiation" will refer to reflected radiation, diffuse radiation, and/or other radiation). For example, the device 200 can detect the presence of glucose and/or measure glucose concentrations in the blood vessel 130. It will be appreciated that the device 200 can collect the radiated radiation as either an absorbance spectrum, an interferogram, or any property associated with the exciting source, such as Raman Scattering, fluorecence, scatter, etc. that would be modified by the presence of the analyte of interest. Other techniques for collecting the radiated radiation may also be used. It will also be appreciated that other chemicals (also referred to as analytes) besides glucose may be detected and/or measured using the device 200.

The device 200 comprises an electronics section 200a and a hood 200b. The electronics section 200a, as will be discussed further in conjunction with FIG. 3–FIG. 5, houses electronics for detecting pattern(s) on an object; selecting a pattern on the object if the object includes more than one pattern; delivering radiation to the object that is coincident with the detected and selected pattern (and/or coincident with an area surrounding or near to the object); and detecting and/or measuring at least one characteristic of the object or of the pattern on the object based the radiated radiation. The electronics section 200a can also include electronics for coagulating or ablating a detected pattern on an object.

The hood 200b covers the object that radiation is to be applied to. For example, the hood 200b can cover the eye 100. The hood 200b can be made of plastic or other suitable material that is impervious to light. Because the hood 200b is impervious to light, it prevents unwanted light radiation from interfering with the pattern detection and radiation application functions of the device 200. The hood 200b can be of a rigid structure or a non-rigid structure. An advantage of using a non-rigid structure is that it enables application to a wide variety of objects having varying dimensions. In an embodiment of the invention, the hood 200b can be custom made according to facial characteristics of an individual so that the hood 200b can securely cover the eye 100 and prevent light radiation from interfering with the pattern detection, radiation delivery, and characteristic detection/measurement functions of the device 200.

Figure 3:
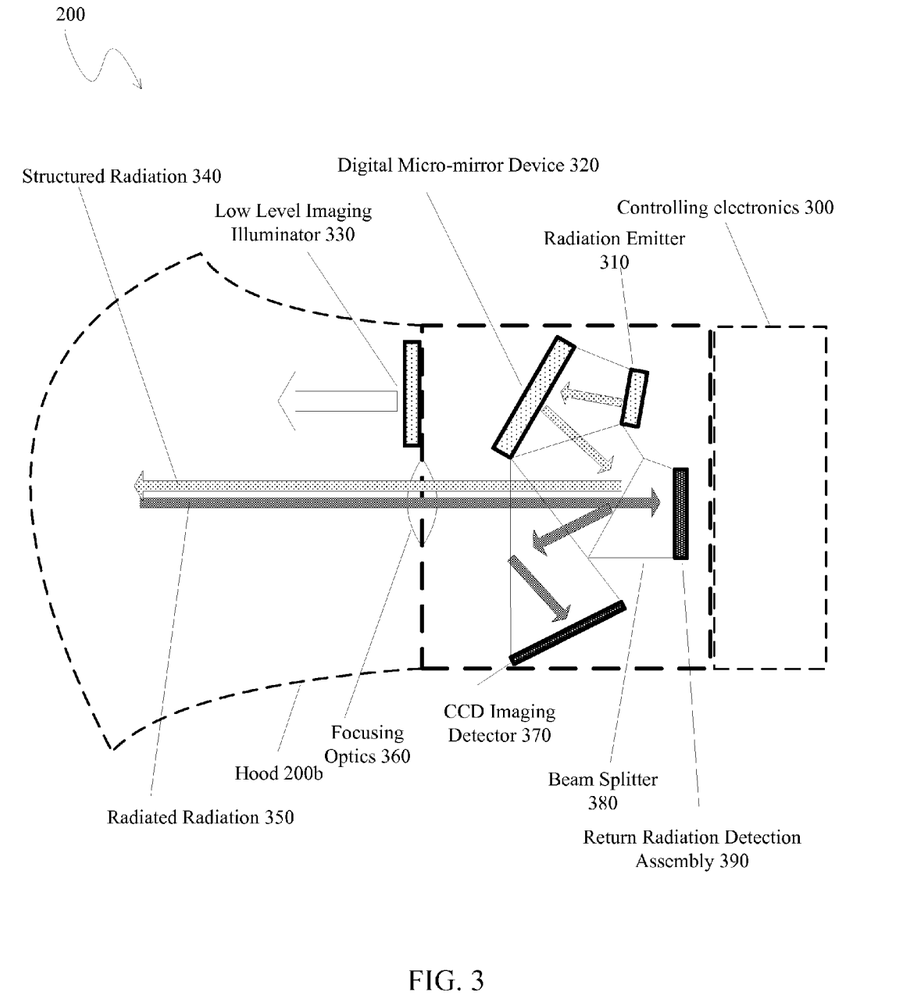
FIG. 3 is a block diagram of the device of FIG. 2.
Figure 4:
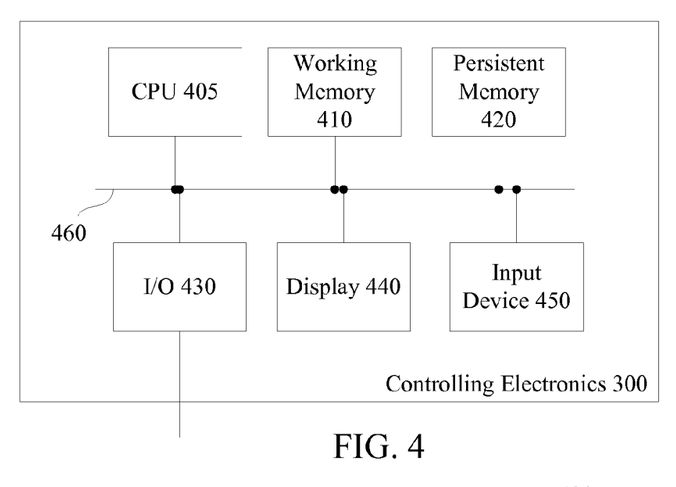
FIG. 4 illustrates a block diagram of the controlling electronics of the device of FIG. 2.
Figure 5:
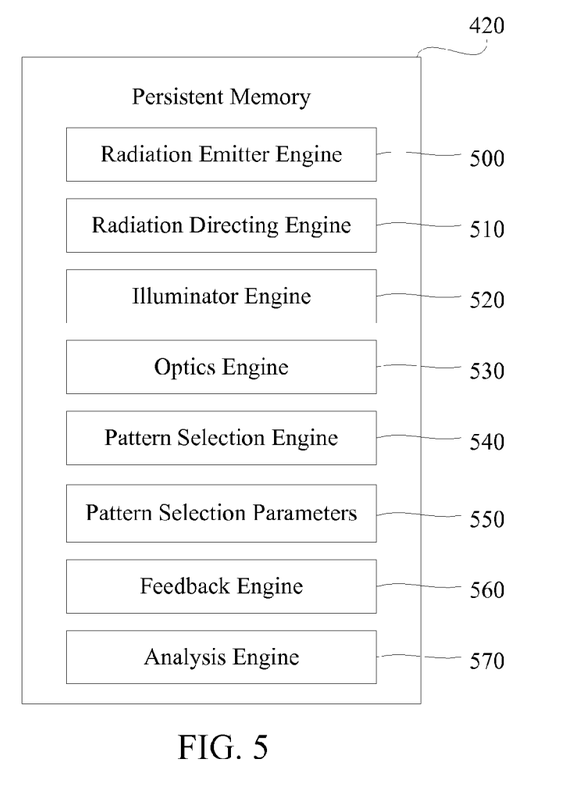
FIG. 5 is a block diagram illustrating the persistent memory of the device of FIG. 2.

FIG. 3 is a block diagram of the device 200. The electronics section 200a includes controlling electronics 300; a radiation emitter 310; a digital micro-mirror device 320 or other radiation directing device; a low level imaging illuminator 330; focusing optics 360; a CCD imaging detector 370; a beam splitter 380; and a return radiation detection assembly 390, such as a pixilated detector. The controlling electronics 300, as will be discussed in further detail in conjunction with FIG. 4 and FIG. 5, is communicatively coupled to the radiation emitter 310; the digital micro-mirror device 320 (or other radiation directing device); the low level imaging illuminator 330; the focusing optics 360; the CCD imaging detector 370; and the return radiation detection assembly 390. Further, the controlling electronics 300 controls the radiation emitter 310; the digital micro-mirror device 320 (or other radiation directing device); the low level imaging illuminator 330; and the focusing optics 360. In an embodiment of the invention, the controlling electronics 300 detects and/or analyzes at least one characteristic (e.g., glucose concentration) of the object that radiation is being applied to based on radiated radiation received by the return radiation detection assembly 390.

The radiation emitter 310 emits structured radiation 340 that is coincident on a pattern detected on an object, such as the blood vessel 130 on the eye 100. In an embodiment of the invention, the radiation emitter 310 emits radiation that is coincident with an area surrounding or near to the pattern, thereby enabling the use of transmissive spectroscopy with diffuse radiation surrounding the pattern. In an embodiment of the invention, the radiation emitted is in the near infra-red spectrum, e.g. about 700 nm to about 3 microns, and is used for spectrum analysis. In another embodiment of the invention, the radiation is of a different wavelength, e.g., about 800 nm, and is used for ablation or coagulation. It will be appreciated that radiation of other wavelengths may be used according to the application. This radiation is reflected by the digital micro-mirror device 320 (which can be made of or coated with aluminum and/or gold and/or other materials), which is controlled by the controlling electronics 300, onto the beam splitter 380, which in turn reflects the radiation through the focusing optics 360 onto a detected pattern on the object (and/or an area surrounding or near to the pattern). It will be appreciated by one of ordinary skill in the art that other techniques may be used for directing radiation emitting by the radiation emitter 310. In another embodiment of the invention, a different radiation directing device may be used in place of the digital micro-mirror device 320. For example, a LCD panel may be used to selectively block radiation emitted by the radiation emitter 310. In another embodiment of the invention, the radiation emitter 310 may itself be the radiation directing device since it can be swivel-mounted to the electronics section 200a, thereby enabling the radiation emitter 310 to direct the radiation onto an object without the need for a mirror 320 or other device.

The low level imaging illuminator 330 emits low level radiation that can be of a different wavelength of the radiation emitted by the radiation emitter 310. Specifically, in an embodiment of the radiation emitted is outside of the critical detection range of the return radiation detection assembly 390 but within the range detectable by the CCD imaging detector 370. For example, the illuminator 330 may include a low level green or blue light emitting diode (LED). An example of suitable radiation that the low level imaging illuminator 330 emits is visible radiation have a wavelength of 500 nm. The low level radiation emitted by the illuminator 330 illuminates an object having a pattern on it.

The controlling electronics 300, in conjunction with the CCD imaging detector 370, use the low level radiation that is reflected from the object to detect a pattern on the object. If there is more than one pattern on the object, the controlling electronics 300 can also select a pattern based on pre-set parameters. Based on the detection and selection, the controlling electronics 300 controls movement of the digital micro-mirror device 320 or other radiation directing device such that radiation emitted by the radiation emitter 310 traces the detected selected pattern on the object. In another embodiment of the invention, the controlling electronics directs a radiation directing device such that radiation emitted by the radiation emitter 310 surrounds or is near to the pattern, but substantially not incident on the pattern itself.

The beam splitter 380 splits radiated radiation 350 into two separate beams. A first beam impacts the return radiation detection assembly 390 and a second beam impacts the CCD imaging detector 370. As mentioned above, the controlling electronics 300 in conjunction with the CCD imaging detector 370, use the reflected radiation to determine the location of the pattern and control the digital micro-mirror device 320 so that radiation emitted by the radiation emitter 310 traces the detected pattern and/or an area surrounding or near to the pattern. The controlling electronics 300 uses the radiation received by the return radiation detection assembly 390 to detect a characteristic and/or analyze characteristics, such as analyte concentration, of the object or pattern on the object using spectrum analysis techniques, as will be discussed in further detail in conjunction with FIG. 6. In an embodiment of the invention, the return radiation detection assembly 390 includes a pixilated detector, thereby enabling spatially determining from where the radiated radiation is from (e.g., which part of the blood vessel radiated the radiation 350).

FIG. 4 illustrates a block diagram of the controlling electronics 300 in an embodiment of the present invention. While other application-specific alternatives might be utilized, it will be presumed for the sake of clarity that the elements comprising the controlling electronics 300 are implemented in hardware, software or some combination thereof by one or more processing systems consistent therewith, unless otherwise indicated.

The controlling electronics includes a central processing unit (CPU) 405; working memory 410; persistent memory 420; input/output (I/O) interface 430; display 440 and input device 450, all communicatively coupled to each other via system bus 460. The CPU 405 may include an Intel PENTIUM microprocessor, a Motorola POWER PC microprocessor, or any other processor capable to execute software stored in the persistent memory 420. The working memory 410 may include random access memory (RAM) or any other type of read/write memory devices or combination of memory devices. The persistent memory 420 may include a hard drive, read only memory (ROM) or any other type of memory device or combination of memory devices that can retain data after the controlling electronics 300 is shut off. The I/O interface 430 is communicatively coupled, via wired or wireless techniques, to the radiation emitter 310; the digital micro-mirror device 320; the low level imaging illuminator 330; the focusing optics 360; the CCD imaging detector 370; and the return radiation detection assembly 390. The display 440 may include a liquid crystal display (LCD) or other display device. The input device 450 may include a keypad or other device for inputting data, or a combination of devices for inputting data. In an embodiment of the invention, the controlling electronics 300 also includes a speaker that can emit aural data. The speaker may be in place of or in addition to the display 440.

One skilled in the art will recognize that the controlling electronics 300 may also include additional devices, such as network connections, additional memory, additional processors, LANs, input/output lines for transferring information across a hardware channel, the Internet or an intranet, etc. One skilled in the art will also recognize that the programs and data may be received by and stored in the controlling electronics 300 in alternative ways.

FIG. 5 is a block diagram illustrating the persistent memory 420. The persistent memory 420 includes a radiation emitter engine 500; a radiation directing engine 510; an illuminator engine 520; an optics engine 530; a pattern selection engine 540; a pattern selection parameters file 550; a feedback engine 560; and an analysis engine 570. The radiation emitter engine 500 controls the radiation emitter 310 including the wavelength of the radiation emitted in an embodiment in which radiation emitter 310 can emit variable wavelength radiation, and the duration of the radiation emission. The radiation directing engine 510, in conjunction with the feedback engine 560, controls the positioning of the digital micro-mirror device 320 or other radiation directing device such that radiation emitted by the radiation emitter 310 traces a detected pattern and/or an area surrounding or near to the detected pattern, such as blood vessel 130, on an object, such as the eye 100.

The illuminator engine 520 controls the functioning of the low level imaging illuminator 330 including the wavelength of the emissions in an embodiment in which the low level imaging illuminator 330 can emit variable wavelengths of radiation, and the duration of the emission. The optics engine 530 controls the focusing optics 360 so that the structured radiation 340 emitted by the radiation emitter 310 is focused on the object, such as the eye 100. The pattern selection engine 540 selects a pattern illuminated by the low level imaging illuminator 330 and imaged on the CCD imaging detector 370. The selection is based on parameters stored in the pattern selection parameters file 550. Examples of parameters could include a pattern within a range of thicknesses and within a range of lengths. It will be appreciated that the parameters can include any number of specifications within pre-specified ranges or having no maximums or minimums.

The feedback engine 560 determines the position of the selected pattern and sends coordinate information to radiation directing engine 510 so that the radiation directing engine 510 can direct radiation emitted by the radiation emitter 310 onto the pattern and/or an area surrounding or near to the pattern. The feedback engine can perform this determination and sending on a very frequent basis, e.g., 200 times/second in one embodiment, so that even if the object is moving, the digital micro-mirror device 320 or other radiation directing device can still track the pattern and therefore the radiation emitted by the radiation emitter 310 remains coincident on the pattern and/or an area surrounding or near to the pattern despite the movement.

The analysis engine 570 detects and/or calculates at least one characteristic of the selected pattern or object based on the radiated radiation 350 received at the return radiation detection assembly 390. In an embodiment of the invention, the analysis engine 570 uses spectrum analysis to determine the concentration of an analyte within the selected pattern. For example, the analysis engine 570 can use spectrum analysis to determine glucose concentration within the blood vessel 130 of the eye 100. The analysis engine 570 can use techniques for spectrum analysis of glucose and other analytes that are described in U.S. Pat. No. 6,061,582, which is hereby incorporated by reference. Other patents that disclose techniques relating to optical detection that analysis engine 570 can use include U.S. Pat. Nos. 6,025,597; 6,026,314; 6,028,311; 6,151,522; 6,181,957; 6,188,477; 6,246,893; and 6,276,798, which are hereby incorporated by reference. Other techniques that analysis engine 570 can use are disclosed in various journal articles that are known to one of ordinary skill in the art. For example, the articles "Spectroscopic and Clinical Aspects of Noninvasive Glucose Measurements" by Omar S. Khalil (Clinical Chemistry 45:2, 1999); "Optical Measurement of Glucose Levels in Scattering Media" by Gilwon Yoon et al. (Proceedings of the 20$^{th}$ Annual International Conference of the IEEE Engineering in Medicine and Biology Society, Vol. 20, No. 4, 1998); and "Multivariate Determination of Glucose Using NIR Spectra of Human Blood Serum" by Fredric M. Ham et al. (IEEE 1994), which are hereby incorporated by reference, disclose techniques that the analysis engine 570 may use.

Figure 6:
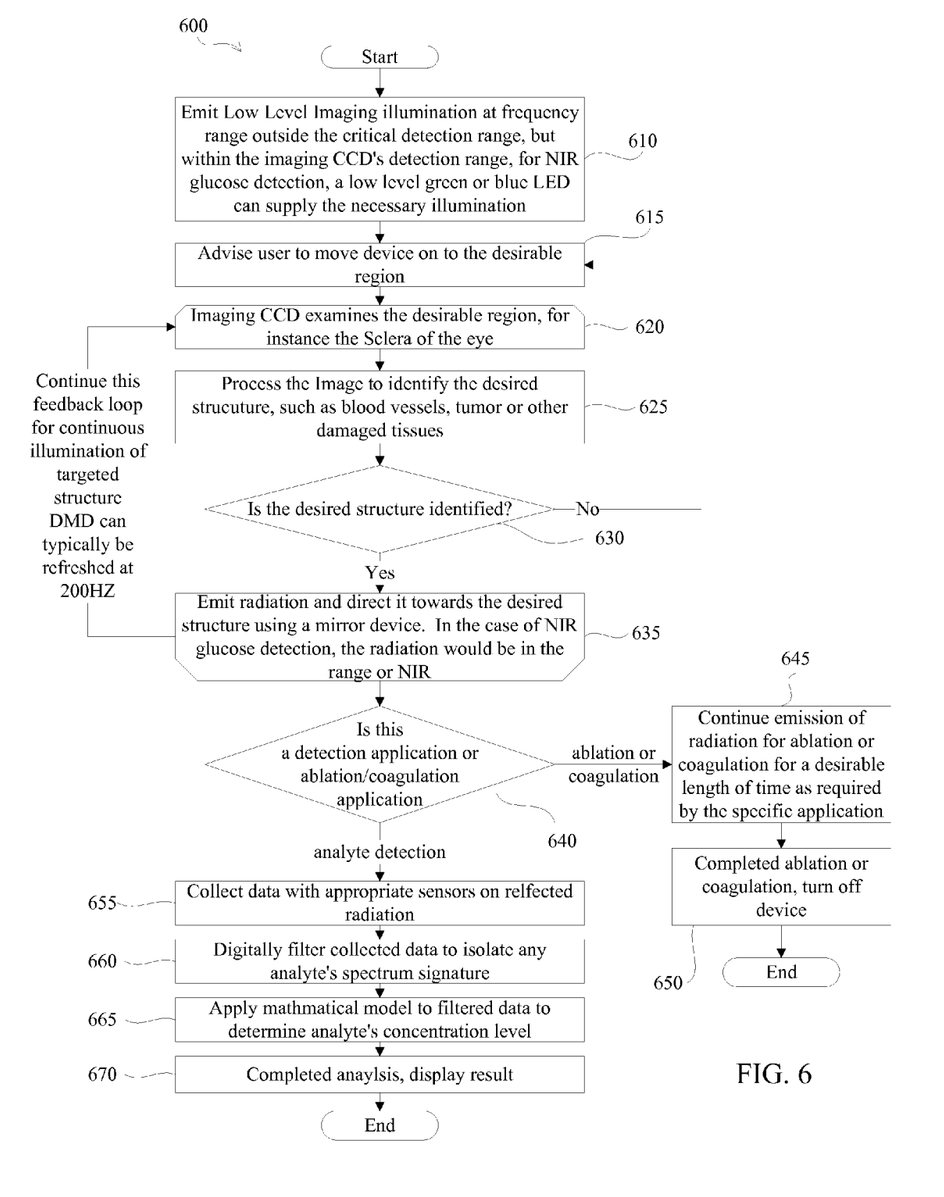
FIG. 6 is a flowchart illustrating a method of pattern delivery of radiation and analysis based on reflected radiation.

FIG. 6 is a flowchart illustrating a method 600 of pattern delivery of radiation and analysis based on reflected radiation. First, low level radiation of a first type is emitted (610). This radiation can be outside the critical detection range, e.g., outside the detection range of the return radiation detector assembly 390, but within the CCD imaging detector 370 detection range. For example, if the return radiation detector assembly 390 detects NIR radiation, then the low level radiation can include light emitted by a low level green or blue LED. Next, the user is advised (615) to position the device hood 200b over the object, e.g., his or her eye. It will be appreciated that the device hood 200b can be placed over any object having a pattern. Further, it will be appreciated that advising (615) need not be including in method 600. It will be further appreciated that advising (615) can be done via aural, visual techniques and/or other techniques (e.g., tactile feedback).

After advising (615), a desired location is examined (620). For example, the sclera or choroid of an eye 100 can be examined (620) for one or more blood vessels. Next, the desired structure or pattern is identified (625). If there is a plurality of patterns, the desired pattern can be identified (625) based on pre-specified parameters, such as thickness, color (e.g., red), and/or length of the pattern. If a pattern is (630) not identified (625), then the advising (615) and examining (620) is repeated until a suitable pattern is identified (625).

After a suitable pattern is identified (625), radiation of a second type is emitted (635) and directed (640) towards the pattern or structure identified (625). The radiation may include radiation for testing (e.g., spectrum analysis) and/or ablation and/or coagulation and/or other purposes. If the radiation is for a testing application, then the radiation can include NIR radiation. If the radiation is for ablation or coagulation, then the radiation should include higher energy radiation, such as radiation having a wavelength of about 800 nm. The process of examining (620), identifying (625) and emitting (635) is repeated at a frequent rate, such as at 200 times/second such that the radiation tracks any movement of the identified pattern. For example, if eye 100 is moving, the examining (620), identifying (625), and emitting (635) will track the blood vessel 130 and continue to impact radiation onto the blood vessel 130 and/or an area surrounding or near to the blood vessel 130 despite the movement.

If (640) this is a coagulation/ablation process, then emission (645) is continued for a suitable amount of time according to the application. After emission (645) is complete, the device 200 is turned (650) off and method 600 ends.

If (640) this is a testing application, then radiated radiation from the emitting (635) is collected (655) and then filtered (660) to isolate a specific analyte's spectrum signature. After filtering (660), a mathematical model is applied (665) to the filtered data to determine concentration of the analyte. The result is then completed (670) and output aurally or visually, e.g., via display 440. Determining analyte concentration, such as glucose concentration, via spectrum analysis is described in U.S. Pat. No. 6,061,582, which is hereby incorporated by reference. The method 600 then ends.

The foregoing description of the illustrated embodiments of the present invention is by way of example only, and other variations and modifications of the above-described embodiments and methods are possible in light of the foregoing teaching. For example, embodiments of the invention can be used for purposes other than glucose monitoring. Further, components of this invention may be implemented using a programmed general purpose digital computer, using application specific integrated circuits, or using a network of interconnected conventional components and circuits. Connections may be wired, wireless, modem, etc. The embodiments described herein are not intended to be exhaustive or limiting. The present invention is limited only by the following claims.

I claim:

1. An apparatus for determining a characteristic of blood, compromising:
    an imaging detector positioned to receive a first type of reflected radiation from an eye;
    a radiation directing device capable of directing a second type of radiation onto a blood vessel of the eye;
    a radiation detection assembly positioned to receive reflected radiation of the second type from the blood vessel; and
    electronics, coupled to the imaging detector, radiation directing device and radiation detection assembly, capable of
        identifying the blood vessel of the eye using reflected radiation data from the imaging detector,
        adjusting the radiation directing device to direct the second type of radiation onto the identified blood vessel, and determining a characteristic of the blood using reflected radiation data from the radiation detection assembly;

wherein the characteristic includes blood glucose levels.

2. The apparatus of claim 1, wherein the electronics identifies the blood vessel by processing the image based on color.

3. The apparatus of claim 1, wherein the radiation directing device includes a digital micro-mirror.

4. The apparatus of claim 1, wherein the second type of radiation includes near infrared radiation.

5. The apparatus of claim 1, wherein the first type of radiation includes blue or green light.

6. The apparatus of claim 1, wherein the electronics is further capable of tracking the identified blood vessel if the blood vessel is moving.

7. The apparatus of claim 1, wherein the radiation detection assembly includes a pixilated detector.

8. A system for determining a characteristic of blood, comprising:

a radiation directing engine capable of adjusting a radiation direction device such that emitted radiation is directed onto a blood vessel of an eye;

a feedback engine, communicatively coupled to the radiation directing engine, capable of determining the position of the blood vessel; and an analysis engine, capable of determining a characteristic of the blood using radiation reflected from the blood vessel;

wherein the characteristic includes blood glucose levels.

9. The system of claim 8, further comprising a pattern selection engine, communicatively coupled to the feedback engine, capable of identifying the blood vessel of the eye.

10. The system of claim 8, wherein the feedback engine is further capable tracking the blood vessel if the blood vessel is moving.

* * * * *